United States Patent [19]

Cavicchioli et al.

[11] Patent Number: 4,937,334

[45] Date of Patent: Jun. 26, 1990

[54] PROCESS FOR THE PREPARATION OF INTERMEDIATES FOR THE SYNTHESIS OF DILTIAZEM

[75] Inventors: Silvia Cavicchioli, Costermano; Maurizio Paiocchi, Milano; Claudio Giordano, Monza, all of Italy

[73] Assignee: Zambon Group S.p.A., Vicenza, Italy

[21] Appl. No.: 384,730

[22] Filed: Jul. 25, 1989

[30] Foreign Application Priority Data

Jul. 26, 1988 [IT] Italy ................................ 21479 A/88

[51] Int. Cl.$^5$ ............................................ C07D 281/10
[52] U.S. Cl. ..................................................... 540/491
[58] Field of Search .......................................... 540/491

[56] References Cited

U.S. PATENT DOCUMENTS

| 3,562,257 | 2/1971 | Kugita et al. | 540/491 |
| 4,438,035 | 3/1984 | Gaino et al. | 540/491 |
| 4,567,175 | 1/1986 | Takeda et al. | 540/491 |

*Primary Examiner*—Robert T. Bond
*Attorney, Agent, or Firm*—Stevens, Davis, Miller & Mosher

[57] ABSTRACT

A process for the preparation of the compound (2S,3S)(+)-3-hydroxy-2,3-dihydro-2-(4-methoxyphenyl)-5-(2-dimethylaminoethyl)-1, 5-benzothiazepin-4(5H)-one is described. Said compound is an intermediate useful in the synthesis of Diltiazem.

9 Claims, No Drawings

PROCESS FOR THE PREPARATION OF INTERMEDIATES FOR THE SYNTHESIS OF DILTIAZEM

The present invention concerns a process for the preparation of the compound (2S,3S)(+)-3-hydroxy-2,3-dihydro-2-(4-methoxyphenyl)-5-(2-dimethylaminoethyl)-1,5-benzothiazepin-4(5H)-one. Said compound is an intermediate for the synthesis of a drug having calcium-antagonist activity known by the international common name of Diltiazem (Merck Index, X Edition, No. 3189, page 466).

Diltiazem of Formula

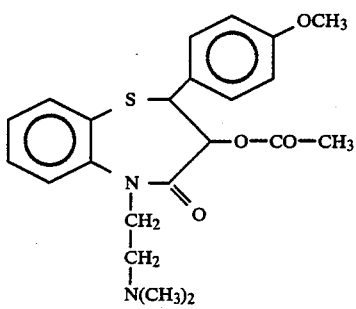

was described by Tanabe Seiyaku in British Patent No. 1,236,467. In said Patent a synthesis is described which, in the last steps, comprises the N-alkylation of the intermediate of formula:

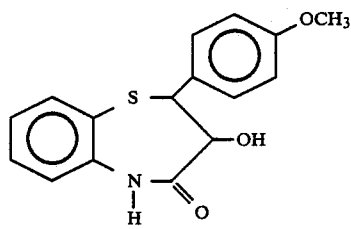

to obtain the corresponding 5-(2-dimethylaminoethyl)-derivative of formula

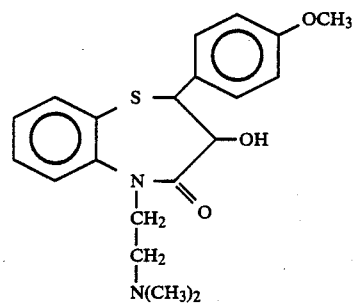

followed by the O-acetylation to obtain the 3-acetyloxy derivative of compound III i.e. Diltiazem.

The alkylation of compound II to obtain compound III, according to British Patent No. 1,236,467, is carried out by transforming compound II in an alkaline salt and by reacting it with 2-dimethylaminoethylchloride

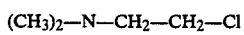 (IV)

In example 6 of the above cited Patent, the only example that describes the preparation of compound III, the product is obtained with yields of about 12%.

Several other processes for the preparation of Diltiazem have been described in the literature and most of them use the same alkylating agent (IV) and carry out the alkylation on compound II or on the corresponding 3-acetyloxy-derivative (for example European Patents No. 81234 and No. 98892 and European Patent Application No. 158303, all in the name of Tanabe). We have now found, and it is the object of the present invention, a process for the preparation of compound (2S,3S)(+)-3-hydroxy-2,3-dihydro-2-(4-methoxyphenyl)-5-(2-dimethylaminoethyl)-1,5-benzothiazepin-4(5H)-one (compound III) by N-alkylation of compound (2S,3S)(+)-3-hydroxy-2,3-dihydro-2-(4-methoxyphenyl)-1,5-benzothiazepin-4(5H)-one (compound II) characterized in that as an alkylating agent 2-dimethylaminoethanol in the presence of methanesulphonyl chloride is used in an inert solvent and in the presence of a base.

As above said compound III is useful as intermediate in the preparation of Diltiazem.

The process object of the present invention consists in reacting compound II with 2-dimethylaminoethanol (V) in the presence of methanesulphonyl chloride in an inert solvent and in the presence of a base.

The reaction parameters can be identified as follows:

Molar ratio between compound V and compound II: at least stoichiometric, preferably with an excess of compound V, e.g. in the molar ration 2:1.

Molar ration between methanesulphonyl chloride and compound II: at least stoichiometric, preferably with an excess of methane-sulphonyl chloride, e.g. 1.3–1.5:1 in mols.

Base: selected from alkaline hydroxides (sodium or potassium) used as such or in aqueous solution.

Solvent: selected from the solvents inert in the reaction conditions. Examples of suitable solvents are aromatic hydrocarbons (benzene, toluene) and chlorinated hydrocarbons (dichloromethane, 1,2-dichloroethane).

Reaction temperature: it is not critical, but the best results are obtained by operating between −10° C. and room temperature.

Reaction time: it depends on various factors but anyhow in 4–20 hours a degree of conversion of compound II higher than 99% is obtained.

Under certain experimental conditions (particularly when benzene or tulene are used as solvent) it can be useful, but not compulsory, to use a catalytic amount of a phase-transfer catalyst in order to increase the reaction rate.

The optional phase-transfer catalyst is preferably a quaternary ammonium salt (e.g. tetrabutylammonium bromide) and it is used in amounts of about 5% by weight with respect to compound II.

By operating within the limits of the above cited experimental conditions compound III is obtained in high yields (also higher than 90%) and in a particularly pure form free from detectable amounts of reaction by-products.

The purity of the obtained product is such that it can be used in the next reaction (O-acetylation to obtain Diltiazem) without further purification or crystallization thereby obtaining analytically pure Diltiazem in accordance with official pharmacopoeia. Moreover it is possible to carry out the acetylation by directly using the solution of compound III obtained by the N-alkylation reaction.

In a practical embodiment compound II and the base are added to a solution or suspension of 2-dimethylaminoethanol and methanesulphonyl chloride in the selected solvent, or vice versa.

The resulting mixture is stirred at a temperature comprised between −10° C. and room temperature for some hours and the disappearance of compound II is analytically monitored.

In a preferred embodiment of the invention, described in detail in Example 1, compound II and an aqueous solution of KOH are added to a suspension of 2-dimethylaminoethanol and methanesulphonyl chloride in methylenechloride.

Alternatively methanesulphonyl chloride may be added to a mixture consisting of compound II, 2-dimethylaminoethanol, organic solvent, potassium hydroxide and optionally water. A three-phase system is obtained (water, methylenechloride and partially undissolved compound II) which is kept under stirring at about 15°-20° C. for 4-6 hours.

The basicity is neutralized and the phases separated. When desired compound III may be isolated by evaporation of the solvent thereby obtaining a pure product which can be directly used for the subsequent O-acetylation or the organic solution of compound III itself may be used.

With respect to the process described in the above cited British patent, the process object of the invention affords sure industrial advantages such as the high yield (higher than 90%), the use of easily available reactants (it is worth noting that 2-dimethylaminoethylchloride is usually prepared from 2-dimethylaminoethanol), the high productiveness and affords compound III in a pure form utilizable without separation or crystallization in the subsequent reaction.

Moreover, as said, the reaction medium is directly compatible with the subsequent reaction.

In order to better illustrate the present invention the following examples are now given.

EXAMPLE 1

Dichloromethane (660 g) and dimethylaminoethanol (29.5 g; 0.031 mol) were introduced under nitrogen in a 1 l flask equipped with mechanical stirring and thermometer.

The obtained solution was cooled at −10° C. and methanesulphonic acid chloride (28.5 g; 0.249 mol) was added in 30 minutes. The temperature of the reaction mixture rose at −5° C.

The obtained suspension was left at −5° C. for further 30 minutes, then (2S,3S)(+)-3-hydroxy-2-(4-methoxyphenyl)-2,3-dihydro-1,5-benzothiazepin-4(5H)-one (50.0 g; 0.166 mol) and, after 1 minute, an aqueous solution (92.4 g) containing potassium hydroxide (31.5 g; 0.563 mol) were added to it under vigorous stirring. After said additions the temperature of the reaction mixture (three-phase system consisting of organic solvent, aqueous phase and undissolved solid product) rose at +5° C. The reaction mixture was heated in 15 minutes up to +15° C. and kept under stirring at that temperature for 5 hours. The diphasic system so obtained was diluted with water (160 g) and additioned with about 190 g of HCl at 3.5% w/v (HCl=0.190 mol) (the final pH of the aqueous phase was 7.5). The phases were separated and the aqueous phase was extracted with dichloromethane (130 g). The organic phases collected together were washed with water (2×50 g) and dried on sodium sulphate. Evaporation of the solvent at reduced pressure afforded an oily crude (61.5 g) whose HPLC analysis showed a content of (2S,3S)(+)-3-hydroxy-2-(4-methoxyphenyl)-2,3-dihydro-5-(2-dimethylaminoethyl)-1,5-benzothiazepin-4(5H)-one (compound III) of 57.2 g (0.154 mol, yield 92.6%).

EXAMPLE 2

The experiment of example 1 was repeafted in an analogous way and with analogous results by using 1,2-dichloroethane as solvent at the temperature of 20° C. for 20 hours obtaining the desired product with 81% yield.

EXAMPLE 3

Methanesulphonic acid chloride (2.85 g, 24.5 mmol) was added in 5 hours to a mixture of compound II (5.0 g, 16.6 mmol) 2-dimethylaminoethanol (2.95 g, 33.1 mmol) dichloromethane (50 ml) and finely polverized solid potassium hydroxide at 90% (3.5 g; 56.3 mmol) kept under nitrogen and magnetically stirred at +18° C. The reaction mixture was left at 18°-20° C. for 12 hours then it was worked up as described in example 1.

The HPLC analysis of the crude (6.35 g) showed that is contained the alkylated product III (4.5 g, 12.1 mmol, molar yield 73%).

What we claim is:

1. A process for the preparation of compound (2S,3S)(+)-3-hydroxy-2,3-dihydro-2-(4-methoxyphenyl)-5-(2-dimethylaminoethyl)-1,5-benzothiazepin-4(5H)-one (compound III) by N-alkylation of compound (2S,3S)(+)-3-hydroxy-2,3-dihydro-2-(4-methoxyphenyl)-1,5-benzothiazepin-4(5H)-one (compound II) with 2-dimethylaminoethanol in the presence of methanesulphonyl chloride in an inert solvent and in the presence of a base.

2. A process according to claim 1 wherein the solvent is selected from aromatic hydrocarbons and chlorinated hydrocarbons.

3. A process according to claim 1 wherein the solvent is dichloromethane.

4. A process according to claim 1 wherein the base is an alkaline hydroxide optionally in aqueous solution.

5. A process according to claim 1 wherein the reaction temperature is comprised between −10° C. and room temperature.

6. A process according to claim 1 wherein the obtained product is not isolated but is directly used in solution for the preparation of Diltiazem.

7. A process according to claim 1 wherein compound II and the base are added to a solution or suspension of 2-dimethylaminoethanol and methanesulphonyl chloride in the selected organic solvent or vice versa.

8. A process according to claim 1 wherein methanesulphonyl chloride is added to a mixture of compound II, 2-dimethylaminoethanol, organic solvent, alkaline hydroxide and optionally water.

9. A process according to claim 1 wherein compound II is reacted with 2-dimethylaminoethanol in the presence of methanesulphonyl chloride in an organic solvent selected from aromatic or chlorinated hydrocarbons in the presence of a base selected from sodium or potassium hydroxide or an aqueous solution thereof and at a temperature comprised between −10° C. and room temperature.

* * * * *